(12) United States Patent
Lim et al.

(10) Patent No.: US 6,344,045 B1
(45) Date of Patent: *Feb. 5, 2002

(54) SIZING AND THERAPEUTIC CATHETER WITH SHEATH

(75) Inventors: Florencia Lim, Union City, CA (US); Christopher L. Haig, Rhode St. Genese (BE); Vidya J. Nayak, Cupertino, CA (US); Joann Heberer, Redwood City, CA (US); Robert D. Ainsworth, Scotts Valley, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/642,961

(22) Filed: Aug. 17, 2000

Related U.S. Application Data

(63) Continuation-in-part of application No. 09/295,694, filed on Apr. 21, 1999, which is a continuation-in-part of application No. 09/063,969, filed on Apr. 21, 1998.

(51) Int. Cl.[7] .................................................. A61F 11/00
(52) U.S. Cl. ........................ 606/108; 606/192; 604/96; 604/101; 604/194
(58) Field of Search ................................ 606/108, 191, 606/192, 194; 604/96, 280, 282, 101, 102, 264, 53

(56) References Cited

U.S. PATENT DOCUMENTS

| | | | | | |
|---|---|---|---|---|---|
| 4,540,404 | A | * | 9/1985 | Wolvek | 604/96 |
| 5,549,551 | A | * | 8/1996 | Peacock, III et al. | 604/96 |
| 5,749,851 | A | * | 5/1998 | Wang | 604/96 |
| 5,843,027 | A | * | 12/1998 | Stone et al. | 604/53 |
| 5,843,092 | A | * | 12/1998 | Heller et al. | 606/108 |

* cited by examiner

*Primary Examiner*—Pedro Philogene
(74) *Attorney, Agent, or Firm*—Coudert Brothers LLP

(57) ABSTRACT

The present invention is directed to a gauging system and method for using the same for determining the size of a lesion within a patient's body prior to stenting the lesion. In one embodiment the gauging system includes a catheter having an elongated shaft with proximal and distal ends, and an outer sheath formed of a compliant material and disposed about at least a portion of the catheter elongated shaft and being slidable over the same. In another embodiment, the gauging system further includes a radially expandable member formed of the same or different compliant material mounted on a distal section of the shaft and has an interior chamber in fluid communication with an inflation lumen extending within at least a portion of a distal shaft section to a location spaced proximally from the shaft distal end.

28 Claims, 3 Drawing Sheets

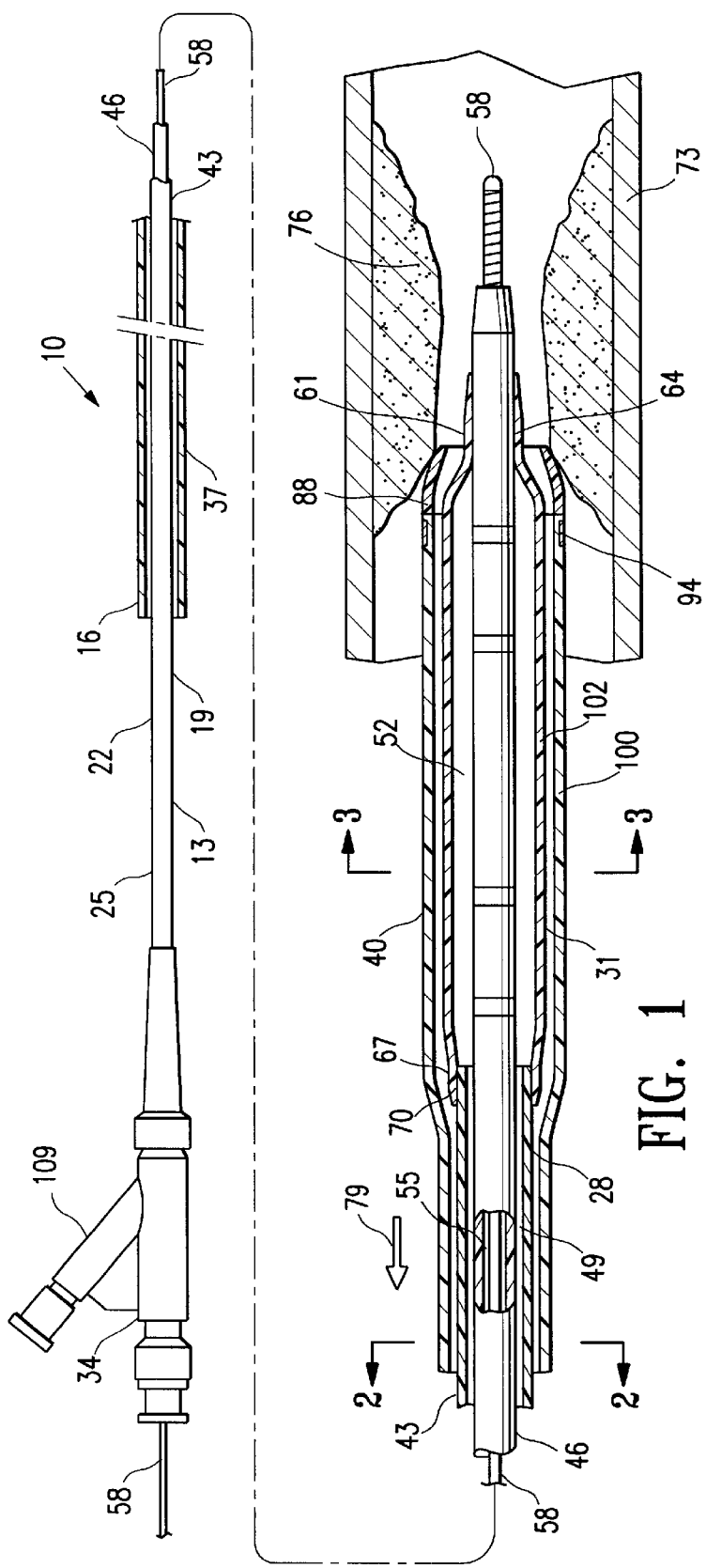
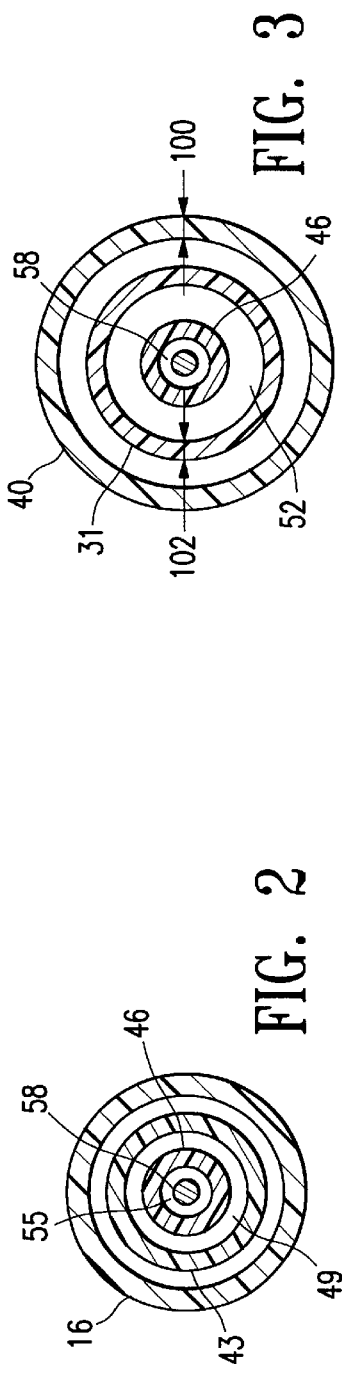
FIG. 1
FIG. 2
FIG. 3

SIZING AND THERAPEUTIC CATHETER WITH SHEATH

RELATED APPLICATIONS

This application is a continuation in part of U.S. patent application, Ser. No. 09/295,694 by Lee et al, entitled "Stent Deploying Catheter Balloon and Balloon Catheter," filed on Apr. 21, 1999; which in turn is a continuation-in-part application of U.S. patent application, Ser. No. 09/063,969 by Lee et al, entitled "Stent Deploying Catheter System," filed on Apr. 21, 1998; both assigned to the assignee of the present invention, and both incorporated herein by reference in their entirety.

FIELD OF INVENTION

This invention relates to the field of intravascular catheters, and more particularly to a balloon catheters.

In percutaneous transluminal coronary angioplasty (PTCA) procedures a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference. Thus, stents are used to open a stenosed vessel, and strengthen the dilated area by remaining inside the vessel.

At times, when either or both using a dilatation balloon catheter or a stent deployment catheter, the physician may have to exchange the catheter more than once due to the size of the catheter not being correct for the intended area of treatment.

Thus, what has been needed is a device that can provide information regarding the appropriate size of catheter. The present invention satisfies this and other needs.

SUMMARY OF THE INVENTION

The present invention is directed to a gauging system and method for using the same for determining the size of a lesion within a patient's body prior to stenting the lesion.

In one embodiment the gauging system includes a catheter having an elongated shaft with proximal and distal ends, and an outer sheath formed of a compliant material and disposed about at least a portion of the catheter elongated shaft and being slidable over the same.

In another embodiment the gauging system includes a catheter having an elongated shaft with proximal and distal ends and inflation lumen extending within at least a portion of a distal shaft section to a location spaced proximally from the shaft distal end, a radially expandable member formed of a first compliant material mounted on the distal shaft section and having an interior chamber in fluid communication with the shaft inflation lumen, and an outer sheath formed of a second compliant material slidably disposed about at least a portion of the catheter elongated shaft and having a distal portion slidably disposed about the expandable member.

The outer sheath and the expandable member may be formed of the same or different compliant materials. The term "compliant" as used herein refers to thermosetting and thermoplastic polymers which exhibit substantial stretching upon the application of tensile force. Additionally, compliant balloons transmit a greater portion of applied pressure before rupturing than non-compliant balloons. Additionally, the term "same material" as used herein includes materials having the same chemical make up with the same or different physical properties (e.g., different durometers).

When the same material having the same chemical make up is used for forming the outer sheath and the expandable member, preferably, the outer sheath has a Shore durometer higher than the material for forming the expandable member. Alternatively, when the material forming the outer sheath and the expandable member have the same chemical make up and physical properties (e.g., Shore durometer), the wall thickness of the outer sheath is at least twice the wall thickness of the expandable member.

Suitable compliant balloon materials include, but are not limited to, elastomeric materials, such as elastomeric varieties of latex, silicone, polyurethane, polyolefin elastomers polyethylene, flexible polyvinyl chloride (PVC), ethylene vinyl acetate (EVA), ethylene methylacrylate (EMA), ethylene ethylacrylate (EEA), styrene butadiene styrene (SBS), ethylene propylene diene rubber (EPDM), polytetraflouroethylene (ePTFE), and Ultra high molecular weight polyethylene (UHMWPE). The presently preferred compliant material has an elongation at failure at room temperature of at least about 250% to about 650%, preferably from about 300% to about 400%, and a Shore durometer of about 45 A to about 75D, preferably about 60A to about 65D. Preferably, the balloon is a wingless balloon. Alternatively, when the balloon is preformed to include folds (or wings), the material forming the balloon should have excellent refold characteristics (such that the sheath can be placed over it), with preferably, a Shore durometer of about 60A to about 75D.

The presently preferred compliant material is a thermoplastic aromatic polyether polyurethane. More preferably, the compliant material has a softening temperature around body temperature (i.e., 37° C.), thus, softening upon insertion into the body, resulting in improved performance. Additionally, balloons and sheaths formed of the present compliant materials are axially substantially non-compliant, i.e., have minimum axial growth as for example when the balloon is inflated, with the axial and radial size of the balloon deflating to the original pre-inflation size following inflation and deflation.

BRIEF DESCRIPTION OF THE DRAWINGS

FIG. 1 is a longitudinal cross sectional view of a balloon catheter having an outer sheath embodying features of the invention.

FIG. 2 is a transverse cross sectional view of the catheter of FIG. 1 taken along line 2—2.

FIG. 3 is a transverse cross sectional view of the catheter of FIG. 1 taken along line 3—3.

DETAILED DESCRIPTION OF THE INVENTION

Figure 4:
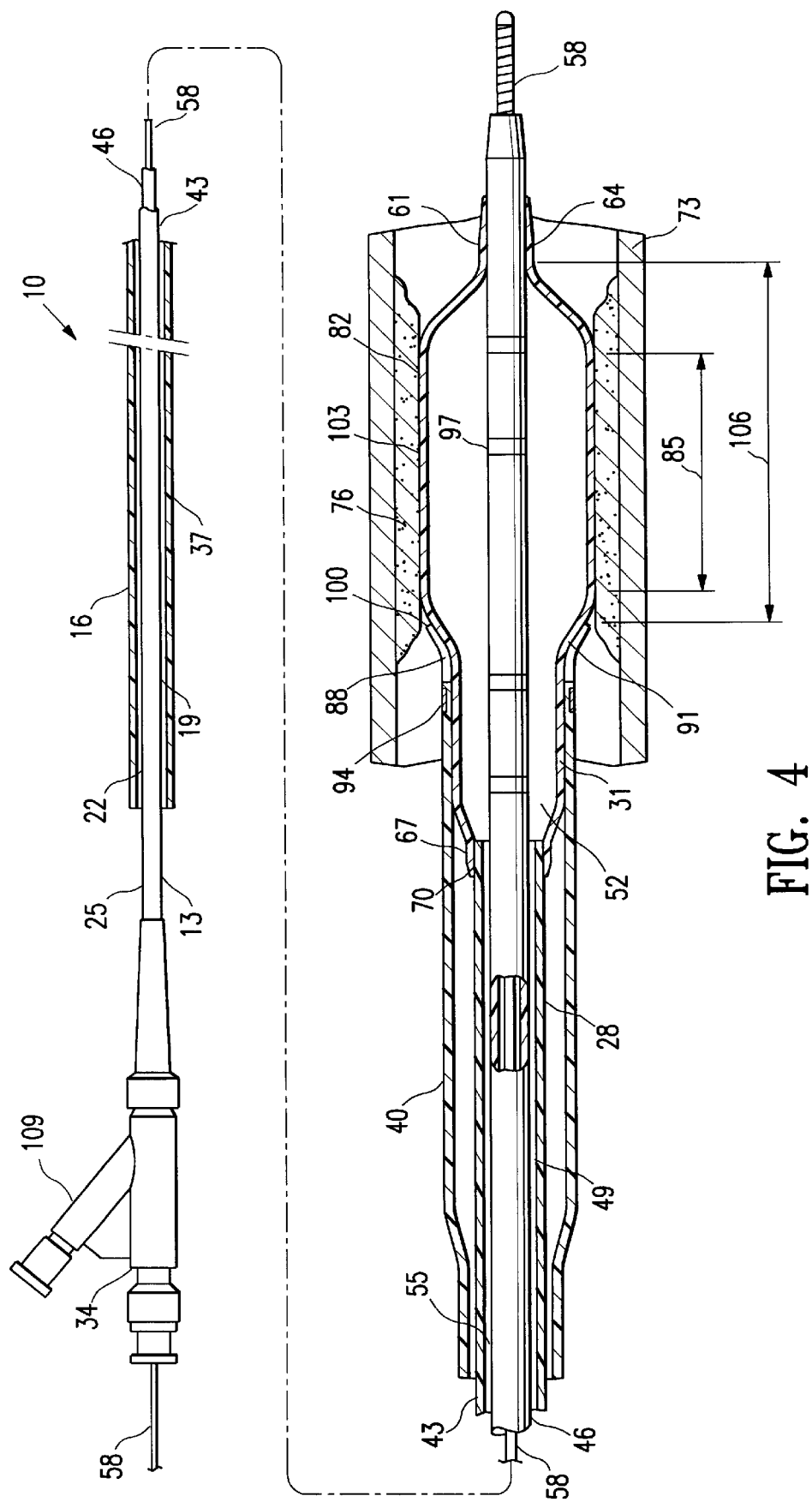
FIG. 4 is a longitudinal cross sectional view of the catheter of FIG. 1 with a portion of the balloon being uncovered for dilating a stenosis.

FIGS. 1 through 3 illustrate an intravascular catheter assembly 10 which embodies features of the invention. The catheter assembly 10 includes a balloon dilatation catheter 13 and an outer sheath 16. The balloon dilatation catheter 13 generally includes a catheter 19 having an elongated catheter shaft 22 having a proximal 25 and a distal 28 section, a radially expansive inflatable balloon 31 on the distal section 28 of the catheter shaft 22, and an adapter 34 mounted on the proximal section 25 of catheter shaft 22. The outer sheath 16 includes an elongated shaft 37 disposed about and slidable over the catheter 19 and an expanded distal portion 40 which is adapted to receive the inflatable balloon 31. To maintain the expanded distal portion 40 of the sheath 16 as small as possible, the interior of the balloon 31 is preferably subjected to a vacuum to form as small a profile as possible as shown in FIG. 3.

The inflatable balloon 31 is formed of radially expansive material that is compliant within the working range of the balloon. The term "compliant" as used herein refers to thermosetting and thermoplastic polymers which exhibit substantial stretching upon the application of tensile force. Additionally, compliant balloons transmit a greater portion of applied pressure before rupturing than non-compliant balloons. Additionally, the term "same material" as used herein includes materials having the same chemical make up with the same or different physical properties (e.g., different durometers).

As best illustrated in FIG. 3, the compliant balloon is essentially wingless and does not require folding into a low profile configuration for insertion into the patient.

In the embodiment illustrated in FIG. 1, the catheter shaft 22 has an outer tubular member 43 and an inner tubular member 46 disposed within the outer tubular member 43 and defining, with the outer tubular member 43, inflation lumen 49. The inflation lumen 49 is in fluid communication with the interior chamber 52 of the inflatable balloon 31. The inner tubular member 46 has an inner lumen 55 extending therein which is configured to slidably receive a guidewire 58 suitable for advancement through a patient's coronary arteries. A distal extremity 61 of the inflatable balloon 31 is sealingly secured to a distal extremity 64 of the inner tubular member 46 and a proximal extremity 67 of the balloon 31 is sealingly secured to a distal extremity 70 of the outer tubular member 43. If desired, the catheter shaft 22 may be of dual lumen design or for example, the balloon as an integral part of the distal outer shaft.

The sheath 16 is slidably disposed about the dilatation catheter 13 so that when the catheter assembly 10 is advanced into the patient's artery 73 to dilate or gauge a stenosis 76, the sheath 16 can be moved in the direction indicated by arrow 79 shown in FIG. 1 to at least partially uncover the balloon 31 so that, when inflation fluid is introduced into the interior 52 of the balloon 31, the uncovered portion 82 of the balloon will expand to dilate the stenosis as shown in FIG. 4. In this manner the effective working length 85 of the balloon 31 can be adjusted to accommodate stenosis of various lengths. Upon the completion of the gauging or dilatation, if necessary, the balloon 31 is deflated and may be pulled completely back into the expanded distal portion 40 of the sheath 16 so that both the dilatation catheter 13 and the sheath 16 of the assembly 10 can be removed together or advanced together to another site for stenotic dilatation or gauging. Alternatively, the sheath 16 and the dilatation catheter 13 can be moved independently. As shown in FIGS. 1 and 4, the sheath 16 has an elastically expandable distal tip 88 which conforms to and, to a certain extent, shapes the proximal end 91 of the inflated portion of balloon 31 when the balloon 31 is inflated. When the balloon 31 is deflated, the expanded distal tip 88 will elastically recoil to essentially its pre-expanded size. A radiopaque marker 94 may be provided on the distal end of sheath 16 to the expandable distal tip 88 which allows the physician to determine fluoroscopically its location within a patient. Additionally, one or more radiopaque markers, such as marker 97, may be provided on the inner tubular member 46 to allow the physician to determine the relative position of a distal end 100 of the sheath 16 with respect to balloon 31. The expandable distal tip 88 may have radiopaque material incorporated therein, e.g. barium salt, in lieu of marker 97.

The balloon 31 and the sheath 16 can be, independently, formed of any compliant material, including thermoplastic and thermosetting polymers. When the same material is used for forming the balloon 31 and the sheath 16, the wall thickness 101 of the sheath 16 is preferably at least about twice the wall thickness 102 of the balloon 31.

Suitable compliant balloon materials include, but are not limited to, elastomeric materials, such as elastomeric varieties of latex, silicone, polyurethane, polyolefin elastomers, polyethylene, flexible polyvinyl chloride (PVC), ethylene vinyl acetate (EVA), ethylene methylacrylate (EMA), ethylene ethylacrylate (EEA), styrene butadiene styrene (SBS), ethylene propylene diene rubber (EPDM), polytetraflouroethylene (ePTFE), and Ultra high molecular weight polyethylene (UHMWPE). The presently preferred compliant material has an elongation at failure at room temperature of at least about 250% to about 650%, preferably from about 300% to about 400%, and a Shore durometer of about 45A to about 75D, preferably about 60A to about 65D. Additionally, the material forming the sheath may have a Shore durometer ranging from 60A to 75D.

The presently preferred compliant polymeric materials include polyurethanes such as TECOTHANES, including 55D (having a flexural modulus of about 18000 psi), 65D (having a flexural modulus of about 26000 psi), and 75D, available from Thermedics; and PELLETHANES, including 55D (having a flexural modulus of about 32000 psi), and 65D, available from Dow Chemical. TECOTHANE is a thermoplastic, aromatic, polyether polyurethane synthesized from methylene disocyanate (MDI), polytetramethylene ether glycol (PTMEG) and 1,4 butanediol chain extender. TECOTHANE is presently the preferred material, with grade 65D being more preferred and having a Shore durometer of 65D, an elongation at break of about 300%, a high tensile strength at yield of about 10,000 psi, and a flexural modulus of about 26,000 psi. However, other suitable material may be used. Balloons and sheaths produced from the TECOTHANE and PELLETHANE materials are particularly preferred because they have softening temperature around body temperature (i.e., 37° C.), thus, softening upon insertion into the body, resulting in improved performance. Additionally, when using TECOTHANE and PELLETHANE materials, the axial growth of the balloon during inflation is minimized (i.e., axially non-compliant) with the axial and radial size of the balloon deflating to the original pre-inflation size following inflation and deflation, so that the deflated balloon and sheath elastically recoil to the pre-inflation size. Other suitable compliant polymeric materials include ENGAGE from DuPont Dow Elastomers (an ethylene alpha-olefin polymer) and EXACT, available from Exxon Chemical, both of which are thermoplastic polymers and are believed to be polyolefin elastomers produced from metallocene catalysts. Other suitable compliant materials include, but are not limited to, elastomeric silicones, latexes, and urethanes. The type of compliant material may be chosen to provide compatibility with the catheter shaft material, to thereby facilitate bonding of the balloon to the catheter.

The balloons and sheaths of the invention can be produced by conventional techniques for producing catheter inflatable members, and may be preformed by stretching a straight tube formed of the compliant material or formed in situ after attachment to the catheter shaft.

The burst pressure of the compliant balloon (at a nominal OD of about 3.0 mm with a double wall thickness of about 1.5–1.8 mils) is about 10 to about 15 atm, and the tensile strength of an American Standard Testing Method (ASTM) "dog-bone" sample cut from a compression molded sheet of material is about 3000 psi to about 7500 psi. The hoop strength, e.g. the product of the burst pressure and the balloon diameter, divided by two times the balloon wall thickness, of a 3.0 mm balloon of the invention is about 10,000 psi to about 20,000 psi. The hoop strength of a 2.5 mm balloon formed from TECOTHANE 1065D is about 18,000 psi. The inflation pressure needed to expand a stent varies depending on the balloon material and stent material and design, but is generally about 6 atm to about 8 atm.

The compliant material may be crosslinked or not, depending upon the material and characteristics required for a particular application. The presently preferred polyurethane materials are not crosslinked. However, other suitable materials, such as the polyolefinic polymers ENGAGE and EXACT, are preferably crosslinked. By crosslinking the compliant material, the final inflated balloon or sheath size can be controlled. Conventional crosslinking techniques can be used including thermal treatment and E-beam exposure. After crosslinking, initial pressurization, expansion, and preshrinking, the balloon and sheath will thereafter expand in a controlled manner to a reproducible diameter in response to a given inflation pressure.

The catheter shaft will generally have the dimensions of conventional dilatation or stent deploying catheters. The length of the catheter 10 may be about 90 cm to about 150 cm, and is typically about 135 cm. The outer tubular member 19 has a length of about 25 cm to about 40 cm, an outer diameter (OD) of about 0.039 in" to about 0.042 in", and an inner diameter (ID) of about 0.032 in". The inner tubular member 20 has a length of about 25 cm to about 40 cm, an OD of about 0.024 in" and an ID of about 0.018 in". The inner and outer tubular members may taper in the distal section to a smaller OD or ID.

The length of the compliant balloon 31 may be about 1 cm to about 4 cm, preferably about 1.5 cm to about 3.0 cm, and is typically about 2.0 cm. In an uninflated or deflated state the balloon diameter is generally about 0.015 in" (0.4 mm) to about 0.08 in" (2 mm), and is typically about 0.037 in" (1 mm), and the double wall thickness is generally about 0.0013 in" (0.03 mm) to about 0.0030 in" (0.08 mm), and is typically about 0.0018 in" (0.03 mm) to about 0.0025 in" (0.06 mm). In an expanded state, the balloon diameter is generally about 0.06 in" (1.5 mm) to about 0.18 in" (4.5 mm), and the double wall thickness is about 0.0005 in" (0.012 mm) to about 0.0025 in" (0.06 mm).

The length of the compliant sheath 16 may be about 75 to about 150 cm, preferably about 125 to about 130 cm. The sheath OD is about the same as the OD of a stent delivery system. Generally the OD of the sheath is about 0.035 in" (0.89 mm) to about 0.045 in" (1.1 mm), and is typically about 0.037 in" (0.9 mm), and the wall thickness is generally about 0.003 in" (0.08 mm) to about 0.008 in" (0.2 mm), and is typically about 0.005 in" (0.1 mm). The sheath ID is about 0.015 in" (0.4 mm) to about 0.08 in" (2 mm), and is typically about 0.027 in" (1 mm). The distal end 100 of the sheath 16 may be tapered to ease insertion into the lesion.

Various designs for dilatation catheters well known in the art may be used in the catheter system of the invention. For example, conventional over-the-wire dilatation catheters for angioplasty usually include a guidewire receiving lumen extending the length of the catheter shaft from a guidewire port in the proximal end of the shaft. Rapid exchange dilatation catheters generally include a short guidewire lumen extending to the distal end of the shaft from a guidewire port located distal to the proximal end of the shaft.

In operation, the catheter 13 is inserted into a patient's vasculature to the desired location which is shown in FIGS. 1 and 4 as a dilated stenotic region 76. If the distal 28 section of the shaft 19 with the sheath 16 in an extended state is unable to cross the lesion, the sheath 16 is retracted to expose the very low profile balloon 31, which is then advanced to cross the lesion. The sheath 16 is positioned to expose a portion 103 having a length 106 of the balloon 31 suitable to the length of the lesion. The exposed portion 103 of the balloon 31 is then dilated to a size at which the sheath 16 will cross the lesion by delivering inflation fluid through the inflation lumen 49 to the compliant balloon 31 through an inflation port 109. The lesion is thereafter accessed, crossed, and stented with a stent delivery system. Because of the balloon's compliant material, it expands radially. Longitudinal growth can be prevented by the inner tubular member 46 or by stretching or axial orientation during processing.

Figure 5:
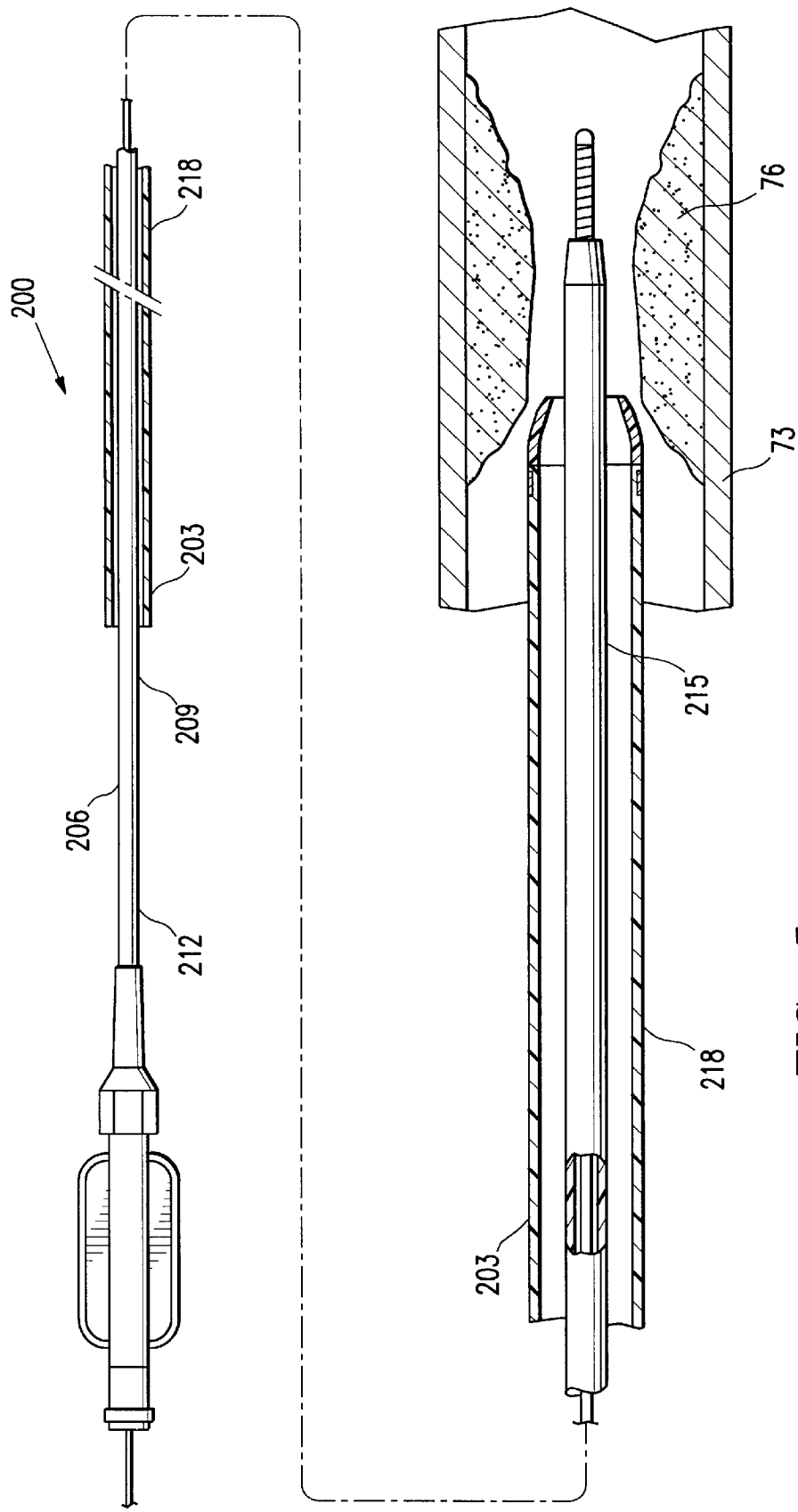
FIG. 5 is a longitudinal cross sectional view of a catheter assembly having a compliant sheath thereon for gauging the lumen diameter of a lesion.

FIG. 5 illustrates another embodiment of a catheter assembly 200 having a compliant sheath 203 thereon for gauging the lumen diameter of the lesion 76. The catheter assembly 200 will be used to assess whether the lesion lumen is accessible by a particular stent delivery system or alternatively requires a pre-dilatation procedure to open the lumen diameter prior to stenting. The catheter assembly 200 includes a catheter 206 and the outer sheath 203. The catheter 206 generally includes an elongated catheter shaft 209 having a proximal 212 and a distal 215 end and constructed on an over the wire, fixed wire, or rapid exchange platform. The outer sheath 203 includes an elongated shaft 218 disposed about and slidable over the catheter 206. The catheter assembly 200 has a distal OD that proximates the OD of a stent delivery system, and further includes a soft tapered distal tip. The outer distal surface of the catheter assembly may have a hydrophilic coating thereon to facilitate lesion access and cross.

In operation, when using the catheter assembly 200, the catheter 203 will be used to gauge the lumen diameter of the lesion prior to crossing with a stent or alternatively, pre-dilating the lesion as may be necessary.

While particular forms of the invention have been illustrated and described, it will be apparent that various modifications can be made without departing from the spirit and scope of the invention. Accordingly, it is not intended that the invention be limited, except as by the appended claims.

What is claimed is:

1. An intravascular gauging system, comprising:
    a catheter having an elongated shaft with proximal and distal ends;
    an outer sheath formed of a compliant material and having a length which is entirely disposed directly about at least a portion of the catheter elongated shaft and being slidable over the same.

2. The system of claim 1 wherein the compliant material has an elongation at failure at room temperature of at least about 500%.

3. The system of claim 1 wherein the compliant material has an elongation at failure at room temperature of at least about 300%.

4. The system of claim 1 wherein the compliant material has a Shore durometer hardness of about 45A to about 75D.

5. The system of claim 1 wherein the compliant material has a Shore durometer hardness of about 60A to about 65D.

6. The system of claim 1 wherein the compliant material is formed of elastomeric material.

7. The system of claim 6 wherein the compliant material is formed of an elastomeric material selected from the group consisting of latex, silicone, polyurethane, polyolefin elastomer, polyethylene, flexible polyvinyl chloride, ethylene vinyl acetate, ethylene methylacrylate, ethylene ethylacrylate, styrene butadiene styrene, ethylene propylene diene rubber, polytetraflouroethylene (ePTFE), and Ultra high molecular weight polyethylene (UHMWPE).

8. The system of claim 1 wherein the compliant material is formed at least in part of a thermoplastic aliphatic or aromatic polyether polyurethane.

9. The system of claim 8 wherein the compliant material has a hoop strength of about 10,000 psi to about 20,000 psi.

10. The system of claim 1 wherein the compliant material is formed at least in part of a polyolefin elastomer.

11. An intravascular gauging system, comprising:
    a catheter having an elongated shaft with proximal and distal ends and inflation lumen extending within at least a portion of a distal shaft section to a location spaced proximally from the shaft distal end;
    an essentially wingless radially expandable uninflated balloon formed of a first compliant material mounted on the distal shaft section and having an interior chamber in fluid communication with the shaft inflation lumen; and
    an outer sheath formed of a second compliant material slidabley disposed about at least a portion of the catheter elongated shaft and having a distal portion slidably disposed about the expandable member.

12. The system of claim 11 wherein the first and the second compliant materials are independently selected from one another.

13. The system of claim 12 wherein the first and the second compliant materials are chemically the same.

14. The system of claim 13 wherein the wall thickness of the outer sheath is at least twice the wall thickness of the expandable member.

15. The system of claim 14 wherein the second compliant material has a Shore durometer higher than the first compliant material.

16. The system of claim 12 wherein the first and second compliant materials have an elongation at failure at room temperature of at least about 250%.

17. The system of claim 12 wherein the first and second compliant materials have an elongation at failure at room temperature of at least about 650%.

18. The system of claim 12 wherein the first and second compliant materials independently have a Shore durometer hardness of about 45A to about 75D.

19. The system of claim 12 wherein the first compliant material forming the expandable member has a Shore durometer hardness of about 60A to about 65D.

20. The system of claim 12 wherein the first and second compliant materials are independently formed of elastomeric material.

21. The system of claim 20 wherein the first and second compliant materials are formed of an elastomeric material independently selected from the group consisting of latex, silicone, polyurethane, polyolefin elastomer, polyethylene, flexible polyvinyl chloride, ethylene vinyl acetate, ethylene methylacrylate, ethylene ethylacrylate, styrene butadiene styrene, ethylene propylene diene rubber, polytetraflouroethylene (ePTFE), and Ultra high molecular weight polyethylene (UHMWPE).

22. The system of claim 12 wherein the first and second compliant materials are independently formed at least in part of a thermoplastic aliphatic or aromatic polyether polyurethane.

23. The system of claim 22 wherein the first and second compliant materials independently have a hoop strength of about 10,000 psi to about 20,000 psi.

24. The system of claim 12 wherein the first and second compliant materials are independently formed at least in part of a polyolefin elastomer.

25. The system of claim 11 wherein the radially expandable member is a wingless balloon.

26. The system of claim 11 wherein the expandable member is easily refoldable.

27. A method for determining the size of a lesion lumen at a location within a patient's body, comprising:
    providing a gauging system, comprising
        a catheter having an elongated shaft with proximal and distal ends;
    an outer sheath formed of a compliant material and having a length which is entirely disposed directly about at least a portion of the catheter elongated shaft and being slidable over the same;
    inserting the gauging system into the patient's body;
    advancing the gauging system to the location; and
    determining the size of the lesion.

28. A method for determining the size of a lesion lumen at a location within a patient's body, comprising:
    providing a gauging system, comprising
        a catheter having an elongated shaft with proximal and distal ends and inflation lumen extending within at least a portion of a distal shaft section to a location spaced proximally from the shaft distal end;

an essentially wingless radially expandable uninflated balloon formed of a first compliant material mounted on the distal shaft section and having an interior chamber in fluid communication with the shaft inflation lumen; and an outer sheath formed of a second compliant material slidably disposed about at least a portion of the catheter elongated shaft and having a distal portion slidably disposed about the expandable member;

inserting the catheter into the patient's body;

advancing the catheter to the location;

retracting the outer sheath in a proximal position to expose at least a portion of the expandable member;

advancing the portion of the catheter having the expandable member there to cross the lesion;

inflating the exposed portion of the expandable member to size allowing the sheath to cross the lesion.

* * * * *

UNITED STATES PATENT AND TRADEMARK OFFICE
CERTIFICATE OF CORRECTION

PATENT NO.    : 6,344,045 B1
DATED         : February 5, 2002
INVENTOR(S)   : Florencia Lim et al.

It is certified that error appears in the above-identified patent and that said Letters Patent is hereby corrected as shown below:

<u>Title page,</u>
Item [56], References Cited, add the following:
--

| | | |
|---|---|---|
| 1,852,351 | 4/1932 | Lewis, |
| 4,540,404 | 9/1985 | Wolvek,. |
| 4,643,194 | 2/1987 | Fogarty, |
| 4,649,922 | 3/1987 | Wiktor, |
| 4,863,440 | 9/1989 | Chin, |
| 4,919,651 | 4/1990 | Doane, |
| 5,092,839 | 3/1992 | Kipperman, |
| 5,108,416 | 4/1992 | Ryan, et al., |
| 5,180,367 | 1/1993 | Kontos, et al., |
| 5,192,296 | 3/1993 | Bhate, et al., |
| 5,242,399 | 9/1993 | Lau, et al, |
| 5,246,421 | 9/1993 | Saab, |
| 5,304,199 | 4/1994 | Myers, |
| 5,366,472 | 11/1994 | Hillstead, |
| 5,492,532 | 2/1996 | Ryan, et al., |
| 5,549,551 | 8/1996 | Peacock, III et al., |
| 5,639,274 | 6/1997 | Fischell, et al., |
| 5,702,410 | 12/1997 | Klunder, et al., |
| 5,843,027 | 12/1998 | Stone, et al., |
| 5,843,092 | 12/1998 | Heller, et al., |
| 5,868,708 | 2/1999 | Hart, et al., |
| 5,876,374 | 3/1999 | Alba, et al. --. |

Signed and Sealed this

Eighth Day of October, 2002

*Attest:*

JAMES E. ROGAN
*Attesting Officer*   *Director of the United States Patent and Trademark Office*